(12) United States Patent
Reichert et al.

(10) Patent No.: US 8,236,063 B2
(45) Date of Patent: Aug. 7, 2012

(54) COLORING AGENT WITH SURFACTANT/EMULSIFIER COMBINATION

(75) Inventors: Anja Reichert, Duesseldorf (DE); Irmgard Bender, Duesseldorf (DE); Mechtild Grunwald, Langenfeld (DE); Astrid Kleen, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/291,405

(22) Filed: Nov. 8, 2011

(65) Prior Publication Data

US 2012/0048288 A1    Mar. 1, 2012

Related U.S. Application Data

(63) Continuation of application No. PCT/EP2010/053659, filed on Mar. 22, 2010.

(30) Foreign Application Priority Data

May 11, 2009    (DE) .......................... 10 2009 003 002

(51) Int. Cl.
*A61Q 5/10*    (2006.01)
(52) U.S. Cl. ............. 8/405; 8/406; 8/435; 8/552; 8/602; 8/611
(58) Field of Classification Search ............... 8/405, 406, 8/435, 552, 602, 611
See application file for complete search history.

(56) References Cited

U.S. PATENT DOCUMENTS 7,442,214 B2 * 10/2008 Legrand ........................... 8/405

FOREIGN PATENT DOCUMENTS

| EP | 2143418 A1 | 1/2010 |
|----|-----------|--------|
| WO | 2006136303 A1 | 12/2006 |
| WO | 2007093271 A2 | 8/2007 |
| WO | 2008022958 A2 | 2/2008 |
| WO | 2010002928 A1 | 1/2010 |

OTHER PUBLICATIONS

Schrader, Karlheinz. Grundlagen und Rezepturen der Kosmetika (Fundamentals and Formulations of Cosmetics), 2, Hüthig Buch Verlag GmbH, Heidelberg 1989.

* cited by examiner

*Primary Examiner* — Eisa Elhilo
(74) *Attorney, Agent, or Firm* — David P. LeCroy

(57) ABSTRACT

Agent for oxidative coloring of keratinic fibers comprising a specific combination of non-ionic emulsifiers with a differing degree of ethoxylation and a specific combination of interfacially active substances comprising at least one anionic, at least one zwitterionic and at least one amphoteric surfactant. The agents provide good coloring characteristics while simultaneously protecting against damage to human hair. In particular the agents allow for colors with high color intensity and an improved gray coverage. The agents also provide significant advantages with regard to viscosity stability during storage and use and an improvement in shear sensitivity.

14 Claims, No Drawings

COLORING AGENT WITH SURFACTANT/EMULSIFIER COMBINATION

CROSS REFERENCE TO RELATED APPLICATIONS

This application is a continuation of International Patent Application No. PCT/EP2010/053659 filed 22 Mar. 2010, which claims priority to German Patent Application No. 10 2009 003 002.6 filed 11 May 2009, both of which are incorporated herein by reference.

The invention provides an agent for oxidative coloring of keratinic fibers, which is distinguished by a specific combination of non-ionic emulsifiers having a differing degree of ethoxylation and a specific combination of interfacially active substances containing at least one anionic, at least one zwitterionic and at least one amphoteric surfactant. Agents according to the invention provide good coloring characteristics while simultaneously protecting against damage to human hair. In particular, the agents provide for colors with high color intensity and an improved gray coverage. Finally, the agents have significant advantages with regard to viscosity stability during storage and use, as well as an improvement in shear sensitivity.

Changing the shape and color of hair is an important area of modern cosmetics. It allows the appearance of the hair to be adapted to both the latest fashion trends and to the personal preferences of the individual. In order to change the color of hairstyles in line with fashion trends or to conceal gray or even white hair with fashionable or natural shades, the consumer turns to color-changing agents. In addition to having the desired coloring capacity, these agents should give rise to the minimum possible damage to the hair and should preferably even have additional conditioning properties.

One skilled in the art is familiar with various coloring systems for the provision of color-changing cosmetic agents, particularly for hair, depending on the coloring process requirements.

For permanent, intense colors with corresponding fastness properties, oxidation coloring agents are used. Such coloring agents conventionally contain oxidation dye precursors known as developer components and coupler components. The developer components form the actual dyes under the influence of oxidizing agents or atmospheric oxygen with one another or by coupling with one or more coupler components. Primary aromatic amines having a further free or substituted hydroxyl or amino group in para- or ortho-position, heterocyclic hydrazones, diaminopyrazole derivatives and 2,4,5,6-tetraminopyrimidine and derivatives thereof are conventionally used as developer components. m-Phenylenediamine derivatives, naphthols, pyridine derivatives, resorcinol and resorcinol derivatives, pyrazolones and m-aminophenols are generally used as coupler components.

For temporary colors, coloring or tinting agents which contain substantive dyes as the coloring component are conventionally used. These are dye molecules which attach directly to the substrate and require no oxidative process to develop the color. These colors are generally significantly more sensitive to shampooing than oxidative colors, such that an often undesired shift in shade or even a visible homogeneous color loss occurs much more quickly.

Finally, another coloring method has attracted great attention. In this method precursors of the natural hair dye melanin are applied to a substrate such as hair. Through oxidative processes they then develop nature-analogous dyes in the hair. With repeated use in particular of agents containing 5,6-dihydroxyindoline it is possible to restore the natural hair color of people with gray hair.

If substrates are to be lightened or bleached, dyes coloring the substrate are mostly decolorized by oxidation using corresponding oxidizing agents such as hydrogen peroxide.

Despite their advantageous coloring characteristics, oxidative hair coloring agents in particular are associated with disadvantages for the user.

Firstly, use of oxidizing agents leads to the development of the actual color, and the basic pH of the agents that is necessary for pigment removal leads to damage to the hair structure and to the hair surface. Secondly, there is still a demand for agents with improved coloring capacity. Development is also focused in particular on agents for improved colors having high intensity and chromaticity, as well as good gray coverage capacity, particularly on hair that has been pretreated in differing ways.

Finally, due to the large number of ingredients used, common hair coloring agents frequently have unsatisfactory rheological properties. These are particularly expressed in viscosity fluctuations during storage and use. Thus, agents which become thicker during storage are associated with problems in removal, dosing and application, while agents which experience a fall in viscosity during storage likewise have unsatisfactory application properties. Finally, it is advantageous to provide agents having improved shear sensitivity.

The present invention therefore attempts to reduce the above disadvantages of oxidative hair coloring agents. The coloring agents should bring about a reduction in damage to the hair. In particular, the hair coloring agents should provide protection against oxidative damage to the hair structure and hair surface. The coloring agents should also have improved rheological properties, expressed in particular in improved viscosity stability and shear sensitivity. Furthermore, the coloring agent should provide improved color intensity and an improved gray coverage in comparison to conventional coloring agents, preferably with a reduction in the pH.

It has now been found that a novel coloring cream basis based on a combination of highly ethoxylated fatty alcohol emulsifiers having different high degrees of ethoxylation and a combination of interfacially active compounds containing at least one anionic surfactant, at least one zwitterionic surfactant and at least one amphoteric surfactant results in coloring agents having high viscosity stability.

The present invention therefore firstly provides an agent for coloring keratinic fibers, particularly human hair, containing in a cosmetic carrier at least one oxidation dye precursor, wherein the agent contains— a) at least one non-ionic emulsifier combination comprising at least two ethoxylated, linear fatty alcohols each having 8 to 22 carbon atoms, at least one of the ethoxylated fatty alcohols having a moderate average degree of ethoxylation of 15 to 35 mol of ethylene oxide and at least one of the ethoxylated fatty alcohols having a high average degree of ethoxylation of 40 to 100 mol of ethylene oxide, and b) at least one combination of interfacially active substances, containing at least one anionic surfactant, at least one zwitterionic surfactant and at least one amphoteric surfactant.

Keratinic fibers here refer to fur, wool, feathers and in particular human hair. Although agents according to the invention are primarily suitable for dyeing keratin fibers, there is nothing in principle to preclude their use in other fields.

Agents according to the invention contain active ingredients in a cosmetic carrier. Within the meaning of the invention this cosmetic carrier is aqueous, alcoholic or aqueous-alcoholic. For the purposes of hair coloring, such carriers include creams, emulsions, gels or surfactant-containing foaming solutions, such as shampoos, foam aerosols or other preparations suitable for use on the hair.

Within the meaning of the present invention aqueous-alcoholic carriers are water-containing compositions containing 3 to 70 wt. % of a $C_1$ to $C_4$ alcohol, based on total weight of the application mixture, particularly ethanol or isopropanol. The agents can additionally contain further organic solvents such as methoxybutanol, ethyl diglycol, 1,2-propylene glycol, n-propanol, n-butanol, n-butylene glycol, glycerol, diethylene glycol monoethyl ether, and diethylene glycol mono-n-butyl ether.

All water-soluble organic solvents are preferred here. An aqueous carrier according to the invention contains at least 30 wt. %, particularly at least 50 wt. % of water, based on total weight of the application mixture.

As a first substantial ingredient, the agent contains at least one emulsifier combination comprising at least two ethoxylated, linear fatty alcohols each having 8 to 22 carbon atoms, wherein at least one of the ethoxylated fatty alcohols has a moderate average degree of ethoxylation of 15 to 35 mol of ethylene oxide and at least one of the ethoxylated fatty alcohols has a high average degree of ethoxylation of 40 to 100 mol of ethylene oxide.

Non-ionic emulsifiers are chosen from ethoxylated, linear fatty alcohols preferably having a chain length of 8 to 22 carbon atoms. According to the invention, an ethoxylated fatty alcohol is an addition product of ethylene oxide with a fatty alcohol wherein the degree of ethoxylation indicates the molar amount of ethylene oxide (EO) added on average per mol of fatty alcohol. Surprisingly, it was found that the combination of at least one ethoxylated fatty alcohol having a moderate average degree of ethoxylation and at least one ethoxylated fatty alcohol having a high average degree of ethoxylation is associated with an improvement in viscosity stability and excellent storage stability of the agents.

Preferred ethoxylated fatty alcohols are ethylene oxide addition products with decanol, lauryl alcohol, isotridecyl alcohol, myristyl alcohol, cetyl alcohol, palmoleyl alcohol, stearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol, brassidyl alcohol and the technical mixtures thereof which form, for example, in the high-pressure hydrogenation of technical methyl esters based on fats and oils or aldehydes from the Roelen oxo synthesis and as a monomer fraction in the dimerization of unsaturated fatty alcohols. Addition products with technical fatty alcohols or mixtures thereof having 12 to 18 carbon atoms, such as coconut, palm, palm kernel or tallow fatty alcohol, particularly coconut and/or tallow fatty alcohol, are particularly preferred.

According to the invention, an ethoxylated fatty alcohol having a moderate average degree of ethoxylation is understood to be an addition product of 15 to 35 mol of ethylene oxide per mol of fatty alcohol. Within the meaning of the invention, an ethoxylated fatty alcohol having a high average degree of ethoxylation is understood to be an addition product of 40 to 100 mol of ethylene oxide per mol of fatty alcohol. Preferred fatty alcohols having a high average degree of ethoxylation have a degree of ethoxylation of 40 to 60, particularly 45 to 55.

Depending on the production method, ethoxylated fatty alcohols according to the invention form as a mixture with a varying distribution of degree of ethoxylation. According to the invention, these emulsifiers are therefore identified by the average degree of ethoxylation. This is conventionally indicated by a number after the fatty alcohol suffix "eth-" in the INCI name.

Preferred ethoxylated fatty alcohols having a moderate average degree of ethoxylation include the commercial products Ceteth-15 (Nikkol BC 15 TX, Nikko Chemicals Co., Ltd.), Laneth-15 (Polychol 15, Croda), Ceteareth-15 (Eumulgin CS 15, Cognis); Laneth-16 (and) Ceteth-16 (and) Oleth-16 (and) Steareth-16 (sold as a mixture under the trade name Solulan 16, Noveon); Oleth-20 (Ritoleth 20, Rita Corp.), Ceteth-20 (Brij 58 SP, Uniqema; Lipocol C 20, Lipo Chemicals Inc.), Ceteareth-20 (Surfac JH 200, Surfachem; Eumulgin B 2, Cognis), Laneth-20 (Polychol 20, Croda); Steareth-21 (Brij 721 P, Uniqema; Eumulgin S 21, Cognis); Ceteareth-23 (Mergital C 23, Cognis), Laureth-23 (Canasol BJ 35, Canamax); Ceteareth-25 (Cremophor A 25, BASF); Ceteareth-27 (Plurafac A 38, BASF); and Ceteareth-30 (Lipocol SC 30, Lipo Chemicals; Eumulgin B 3, Cognis).

Preferred ethoxylated fatty alcohols having a high average degree of ethoxylation include the commercial products: Ceteth-40 (Nikkol BC 40 TX, Nikko Chemicals Co., Ltd.), Laneth-40 (Polychol 40, Croda); Oleth-50 (Nikkol BO 50 V, Nikko Chemicals Co., Ltd.), Ceteareth-50 (Genapol T 500, Clariant; Mergital CS 50, Cognis); Ceteareth-60 (Findet 1618 A 72, KAO Corp.); and Ceteareth-80 (Lutensol AT 80, BASF). Ceteareth-50 is particularly preferred.

Ethoxylated fatty alcohols having a moderate and high average degree of ethoxylation are included in the ready-to-use agent in a total amount of from 0.05 to 15 wt. %, preferably 0.1 to 10 wt. %.

Particularly preferred agents according to the invention are those wherein the weight ratio of ethoxylated fatty alcohols having a moderate average degree of ethoxylation to ethoxylated fatty alcohols having a high average degree of ethoxylation in the coloring agent (a) has a value of 3:1 to 1:5, preferably 2:1 to 1:3.

As a further substantial ingredient, agents according to the invention contain at least one combination of interfacially active substances comprising at least one anionic surfactant, at least one zwitterionic surfactant and at least one amphoteric surfactant.

Suitable anionic surface-active substances have a water-solubilizing anionic group such as a carboxylate, sulfate, sulfonate or phosphate group and a lipophilic alkyl group having approximately 8 to 30 C atoms. The molecule can additionally contain glycol or polyglycol ether groups, ester, ether and amide groups and hydroxyl groups. Examples of suitable anionic surfactants, each in the form of the sodium, potassium and ammonium salts as well as the mono-, di- and trialkanolammonium salts having 2 to 4 C atoms in the alkanol group, are— linear and branched fatty acids having 8 to 30 C atoms (soaps), ether carboxylic acids of the formula $RO(CH_2CH_2O)_x CH_2COOH$, wherein R is a linear alkyl group having 8 to 30 C atoms and x=0 or a number from 1 to 16, acyl sarcosides, acyl taurides and/or acyl isethionates each having 8 to 24 C atoms in the acyl group, sulfosuccinic acid mono- and dialkyl esters having 8 to 24 C atoms in the alkyl group and sulfosuccinic acid monoalkyl polyoxyethyl esters having 8 to 24 C atoms in the alkyl group and 1 to 6 oxyethyl groups, linear alkane sulfonates, linear α-olefin sulfonates and sulfonates of unsaturated fatty acids each having 8 to 24 C atoms and optionally 1 to 6 double bonds, α-sulfo fatty acid methyl esters of fatty acids having 8 to 30 C atoms, alkyl sulfates and alkyl ether sulfates of the formula RO(CH$_2$CH$_2$O)$_x$SO$_3$H, wherein R is preferably a linear alkyl group having 8 to 30 C atoms and x=0 or 1 to 12, mixtures of surface-active hydroxylsulfonates, sulfated hydroxyalkyl polyethylene and/or hydroxyalkylene propylene glycol ethers, esters of tartaric acid and citric acid with alcohols which are addition products of approximately 2 to 15 molecules of ethylene oxide and/or propylene oxide with fatty alcohols having 8 to 22 C atoms, alkyl and/or alkenyl ether phosphates of the formula

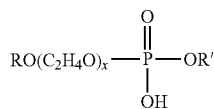

wherein R preferably is an aliphatic, optionally unsaturated, hydrocarbon residue having 8 to 30 carbon atoms, R' is hydrogen, a (CH$_2$CH$_2$O)$_y$R residue, and x and y independently of each other are a number from 1 to 10, sulfated fatty acid alkylene glycol esters of the formula RC(O)O(alkO)$_n$SO$_3$H, wherein R is a linear or branched, aliphatic, saturated and/or unsaturated alkyl residue having 6 to 22 C atoms, alk is CH$_2$CH$_2$, CHCH$_3$CH$_2$ and/or CH$_2$CHCH$_3$ and n is a number from 0.5 to 5, monoglyceride sulfates and monoglyceride ether sulfates.

In particular, the coloring agents according to the invention contain anionic surfactants selected from fatty acids, alkyl sulfates, alkyl ether sulfates and ether carboxylic acids with 10 to 18 C atoms in the alkyl group and up to 12 glycol ether groups in the molecule.

Surface-active compounds classified as zwitterionic surfactants are those bearing at least one quaternary ammonium group and at least one carboxylate, sulfonate or sulfate group in the molecule. Particularly suitable zwitterionic surfactants are betaines such as N-alkyl-N,N-dimethylammonium glycinates, for example, cocoalkyl dimethylammonium glycinate, N-acyl aminopropyl-N,N-dimethylammonium glycinates, for example cocoacylaminopropyl dimethylammonium glycinate, and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known under the INCI name Cocamidopropyl Betaine.

Preferred amphoteric surfactants are compounds according to formula (I) and/or physiologically tolerable salts thereof,

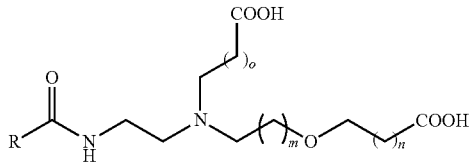

wherein R is a linear or branched, saturated or unsaturated C$_{10}$-C$_{22}$ alkyl group; and m, n and o independently of one another are a whole number 1, 2 or 3. In a preferred embodiment, R is a linear C$_{12}$-C$_{18}$ alkyl group. Particularly preferred compounds of formula (I) are sold under the INCI name Disodium Cocoamphodipropionate with the trade name Miranol C2M SF conc. (Rhodia), Amphoterge K-2 (Lonza) and Monateric CEM-38 (Unichema). The R—CO— group according to formula (I) is derived from fatty acids of coconut oil.

One embodiment of the present invention is one wherein the combination of interfacially active substances consists of:
at least alkyl ether sulfate as the anionic surfactant;
at least Cocamidopropyl Betaine as the zwitterionic surfactant; and
at least Disodium Cocoamphodipropionate as the amphoteric surfactant.

A further embodiment of the present invention is one wherein the combination of interfacially active substances consists of:
at least alkyl sulfate as the anionic surfactant;
at least Cocamidopropyl Betaine as the zwitterionic surfactant; and
at least Disodium Cocoamphodipropionate as the amphoteric surfactant.

A further embodiment of the present invention is one wherein the combination of interfacially active substances consists of:
at least one ether carboxylic acid as the anionic surfactant;
at least Cocamidopropyl Betaine as the zwitterionic surfactant; and
at least Disodium Cocoamphodipropionate as the amphoteric surfactant.

Finally, a further embodiment of the present invention is one wherein the combination of interfacially active substances consists of:
at least one fatty acid as the anionic surfactant;
at least Cocamidopropyl Betaine as the zwitterionic surfactant; and
at least Disodium Cocoamphodipropionate as the amphoteric surfactant.

Anionic, amphoteric and zwitterionic surfactants are preferably present in the agent in an amount of 0.05 to 30 wt. %, more preferably 0.1 to 20 wt. %, based on total weight of the agent.

An embodiment of the present invention has the characterizing feature that the combination of interfacially active substances has a weight ratio of total anionic surfactants to total amphoteric and zwitterionic surfactants with a value of from 3 to 0.3, preferably from 2 to 0.5, based on total weight of the ready-to-use agent.

Finally, agents according to the invention contain at least one oxidation dye precursor. Thus, the agents for coloring keratinic fibers contain at least one oxidation dye precursor of the developer type and/or coupler type. Coloring agents according to the invention preferably contain at least one oxidation dye precursor of the developer type and at least one oxidation dye precursor of the coupler type.

The oxidation dye precursors are preferably used in an amount from 0.005 to 20 wt. %, more preferably from 0.05 to 5 wt. % and particularly preferably from 0.1 to 5 wt. %, based on the ready-to-use oxidation coloring agent.

Developer and coupler components are conventionally used in free form. In the case of substances containing amino groups, however, it can be preferable to use them in salt form, particularly in the form of hydrochlorides and hydrobromides or sulfates. Developer components and coupler components are generally used in approximately molar amounts to one another.

Even if the molar use has proved convenient, a certain excess of individual oxidation dye precursor is not disadvantageous, so that developer components and coupler components can be included in a molar ratio of 1:0.5 to 1:2.

Suitable developer components include p-phenylenediamine derivatives chosen in particular from one or more compounds of p-phenylenediamine, p-toluoylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis-(2-hydroxyethyl)-p-phenylenediamine, 4-N,N-bis-(2-hydroxyethyl)amino-2-methylaniline, 4-N,N-bis-(2-hydroxyethyl)amino-2-chloroaniline, 2-(2-hydroxyethyl)-p-phenylenediamine, 2-(1,2-dihydroxyethyp-p-phenylenediamine, 2-fluoro-p-phenylenediamine, 2-isopropyl-p-phenylenediamine, N-(2-hydroxypropyl)-p-phenylenediamine, 2-hydroxymethyl-p-phenylenediamine, N,N-dimethyl-3-methyl-p-phenylenediamine, N-ethyl-N-2-hydroxyethyl-p-phenylenediamine, N-(2,3-dihydroxypropyl)-p-phenylenediamine, N-(4'-aminophenyl)-p-phenylenediamine, N-phenyl-p-phenylenediamine, 2-(2-hydroxyethyloxy)-p-phenylenediamine, 2-methoxymethyl-p-phenylenediamine, 2-(2-acetylaminoethyloxy)-p-phenylenediamine, N-(2-methoxyethyl)-p-phenylenediamine, N-(4-amino-3-methylphenyl)-N-[3-(1H-imidazol-1-yl)propyl]amine, 5,8-diaminobenzo-1,4-dioxane and the physiologically tolerable salts thereof. Preferred phenylenediamine derivatives are chosen from at least one compound from p-phenylenediamine, p-toluoylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazol-1-yl)propyl]amine, 2-methoxymethyl-p-phenylenediamine and the physiologically tolerable salts of these compounds.

It can furthermore be preferable according to the invention to use as the developer component compounds containing at least two aromatic nuclei which are substituted with amino and/or hydroxyl groups. Preferred binuclear developer components are chosen from at least one of the following compounds: N,N'-bis-(2-hydroxyethyl)-N,N'-bis-(4'-aminophenyl)-1,3-diaminopropan-2-ol, N,N'-bis-(2-hydroxyethyl)-N,N'-bis-(4'-aminophenyl)ethylenediamine, N,N'-bis-(4'-aminophenyl)tetramethylenediamine, N,N'-bis-(2-hydroxyethyl)-N,N'-bis-(4'-aminophenyl)tetramethylenediamine, N,N'-bis-(4-(methylamino)phenyl)tetramethylenediamine, N,N'-diethyl-N,N'-bis-(4'-amino-3'-methylphenyl)ethylenediamine, bis-(2-hydroxy-5-aminophenyl)methane, N,N'-bis-(4'-aminophenyl)-1,4-diazacycloheptane, N,N'-bis-(2-hydroxy-5-aminobenzyl)piperazine, N-(4'-aminophenyl)-p-phenylenediamine and 1,10-bis-(2',5'-diaminophenyl)-1,4,7,10-tetraoxadecane and the physiologically tolerable salts thereof. Particularly preferred binuclear developer components are chosen from N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane or one of the physiologically tolerable salts of these compounds.

It can also be preferable according to the invention to use a p-aminophenol derivative or one of its physiologically tolerable salts as the developer component. Preferred p-aminophenols are in particular p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(2-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(2-hydroxyethylaminomethyl)phenol, 4-amino-2-(1,2-dihydroxyethyl)phenol, 4-amino-2-fluorophenol, 4-amino-2-chlorophenol, 4-amino-2,6-dichlorophenol, 4-amino-2-(diethylaminomethyl)phenol and physiologically tolerable salts thereof. Particularly preferred compounds are p-aminophenol, 4-amino-3-methylphenol, 4-amino-2-aminomethylphenol, 4-amino-2-(1,2-dihydroxyethyl)phenol and 4-amino-2-(diethylaminomethyl)phenol.

The developer component can also be chosen from o-aminophenol and derivatives thereof, such as 2-amino-4-methylphenol, 2-amino-5-methylphenol or 2-amino-4-chlorophenol.

The developer component can furthermore be chosen from heterocyclic developer components, such as pyrimidine derivatives, pyrazole derivatives, pyrazolopyrimidine derivatives, pyrazolopyrazole derivatives and physiologically tolerable salts thereof. Preferred pyrimidine derivatives are in particular the compounds 2,4,5,6-tetraminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine. Preferred pyrazole derivatives are in particular the compounds selected from 4,5-diamino-1-methylpyrazole, 4,5-diamino-1-(2-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-t-butyl-3-methylpyrazole, 4,5-diamino-1-(2-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2-aminoethyl)amino-1,3-dimethylpyrazole, and the physiologically tolerable salts thereof. Of the pyrazolo[1,5-a]pyrimidines, pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethyl-pyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)-(2-hydroxyethyl)amino]ethanol; 2-[(7-aminopyrazolo[1,5-a]pyrimidin-3-yl)-(2-hydroxyethyl)amino]ethanol; 5,6-dimethylpyrazolo[1,5-a]pyrimidin-3,7-diamine; 2,6-dimethylpyrazolo[1,5-a]pyrimidine-3,7-diamine; 3-amino-7-dimethylamino-2,5-dimethylpyrazolo[1,5-a]pyrimidine as well as the physiologically tolerable salts thereof and tautomeric forms thereof, if a tautomeric equilibrium exists, are suitable in particular. Preferred pyrazolopyrazole derivatives are 2,3-diamino-6,7-dihydro-1H,5H-pyrazolo[1,2-a]pyrazol-1-one and 2,3-diamino-6,7-dihydro-8,8-dimethyl-1H,5H-pyrazolo[1,2-a]pyrazol-1-one.

Particularly preferred developer components are chosen from at least one compound from p-phenylenediamine, p-toluoylenediamine, 2-(2-hydroxyethyl)-p-phenylenediamine, dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N, N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one and the physiologically tolerable salts of these compounds.

The developer components are preferably used in an amount from 0.005 to 20 wt. %, preferably 0.1 to 5 wt. %, based on total weight of the ready-to-use oxidation coloring agent.

In the context of oxidative dyeing, coupler components develop no significant color on their own but always need the presence of developer components. It is therefore preferable according to the invention that, when at least one coupler component is used, at least one developer component is additionally used.

Coupler components within the meaning of the invention permit at least one substitution of a chemical residue of the coupler with the oxidized form of the developer component. A covalent bond forms between the coupler and developer component in this process. Couplers are preferably cyclic compounds bearing at least two groups on the cycle, chosen from (i) optionally substituted amino groups and/or (ii) hydroxyl groups. If the cyclic compound is a six-membered ring (preferably aromatic), the groups are preferably in ortho-position or meta-position to one another.

Coupler components according to the invention are m-aminophenol and/or derivatives thereof, preferably chosen from at least one compound from m-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-(diethylamino)phenol, N-cyclopentyl-3-aminophenol, 1,3-dihydroxy-5-(methylamino)benzene, 3-ethylamino-4-methylphenol, 2,4-dichloro-3-aminophenol and the physiologically tolerable salts of these compounds.

Coupler components according to the invention are m-diaminobenzene or derivatives, chosen in particular from at least one compound from m-phenylenediamine, 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2'-hydroxyethyl)aminobenzene and the physiologically tolerable salts of the cited compounds.

Coupler components according to the invention are o-diaminobenzenes chosen from at least one compound from 3,4-diaminobenzoic acid and 2,3-diamino-1-methylbenzene and the physiologically tolerable salts of all aforementioned compounds.

Coupler components of the di- or trihydroxybenzene type and derivatives thereof are chosen from at least one compound from resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene.

Coupler components according to the invention are furthermore pyridine derivatives, preferably chosen from at least one compound from 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 3,4-diaminopyridine, 2-(2-methoxyethyl)amino-3-amino-6-methoxypyridine, 2-(4'-methoxyphenyl)amino-3-aminopyridine, and the physiologically tolerable salts of the aforementioned compounds.

Coupler components according to the invention are furthermore naphthalene derivatives containing at least one hydroxyl group, chosen in particular from at least one compound from 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene.

Coupler components according to the invention are indole derivatives and indoline derivatives, preferably chosen from at least one compound from 4-hydroxyindole, 6-hydroxyindole, 7-hydroxyindole, 4-hydroxyindoline, 6-hydroxyindoline and 7-hydroxyindoline and the physiologically tolerable salts of the aforementioned compounds.

Coupler components according to the invention are furthermore pyrimidine derivatives, chosen in particular from at least one compound from 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine and the physiologically tolerable salts of the aforementioned compounds.

Coupler components according to the invention are finally o-aminophenol derivatives such as o-aminophenol, pyrazolone derivatives such as 1-phenyl-3-methylpyrazol-5-one, morpholine derivatives such as 6-hydroxybenzomorpholine or 6-aminobenzomorpholine, quinoxaline derivatives such as 6-methyl-1,2,3,4-tetrahydroquinoxaline and the physiologically tolerable salts of the aforementioned compounds.

Preferred coupler components according to the invention are chosen from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically tolerable salts of the aforementioned compounds.

Coupler components are preferably used in an amount from 0.005 to 20 wt. %, more preferably 0.1 to 5 wt. %, based on total weight of the ready-to-use coloring agent.

Suitable agents according to the invention can additionally contain at least one polymeric thickener. In this way, the rheology of the agents can be converted into creamy/free-flowing systems desired by the consumer.

The polymeric thickener is preferably a hydrophilic thickener. Such thickeners are known to one skilled in the art. Useful polymeric thickeners according to the invention are, inter alia—
- synthetic polymers, particularly polyacrylic acid polymers (carbomers), particularly poly(meth)acrylates, furthermore optionally branched homopolymers or copolymers of acrylic acid, salts thereof or alkyl esters thereof, which are optionally cationically or anionically modified in the alkyl chain; polyacrylamide polymers, in particular homopolymers or copolymers of acrylic acid amide and/or methacrylic acid amide, which are optionally cationically or anionically modified; and copolymers of acrylic acid and acrylic acid amide;
- polysaccharide polymers such as algin, alginates, glucanes such as dextran, pullulan, curdlan, cellulose, laminarin, amylose or lichenin, tragacanth, karaya gum, ghatti gum, agar, carrageenan, chitin, chitosan, gum arabic, gellan, carob gum, galactomannans such as guar or carob seed meal, tamarind kernel powder or derivatives thereof;
- inorganic thickeners, particularly suitable electrolytes such as sodium chloride or potassium chloride, phyllosilicates (polymeric, crystalline sodium disilicates) and magnesium aluminum silicates or bentonites, particularly smectites, such as montmorillonite or hectorite, which can optionally also be suitably modified;

and mixtures thereof.

It has been found that thickening polysaccharide polymers in particular result in gentle formulations which are stable in storage. Preferred polymeric thickeners according to the invention are therefore thickening polysaccharide polymers. Particularly preferred polysaccharides are polymers based on cellulose. Chemically modified celluloses such as acetyl, methyl or ethyl celluloses, hydroxyalkyl celluloses or carboxyalkyl celluloses can be used here. Particularly preferred cellulose derivatives have saccharide side chains, such as xanthan.

In one embodiment of the present invention the polymeric thickener in the agent is a polysaccharide polymer, preferably xanthan.

Preferred agents comprise the polymeric thickener in a total amount of 0.005 to 1.0 wt. %, particularly 0.01 to 0.5 wt. % and most particularly 0.05 to 0.3 wt. %, based on total weight of the application preparation.

In order to protect the keratin fibers and also the skin as far as possible, it is not desirable to establish too high a pH. A further substantial aspect of agents according to the invention is therefore that the ready-to-use hair coloring preparation has a pH in the range from 7 to 11. Use of the hair coloring agents in a weakly alkaline environment is particularly preferred, preferably at a pH in the range from 7.5 to 9.5. The pH values according to the present invention are pH values measured at a temperature of 25° C.

Common acidifying and alkalizing agents for adjusting the pH are familiar to one skilled in the art. Alkalizing agents which can be used to establish the preferred pH can be chosen from basic amino acids, amines, ammonia, alkali metal hydroxides, alkali metal metasilicates, alkali metal phosphates and alkali metal hydrogen phosphates. Preferred acidifying agents according to the invention are food acids such as citric acid, acetic acid, malic acid or tartaric acid, as well as dilute mineral acids. It has been found that agents containing two different alkalizing agents are particularly suitable, especially if one of them is a basic amino acid.

A further embodiment of the agent according to the invention contains a combination of at least two alkalizing agents, wherein at least one alkalizing agent is an alkanol amine chosen from monoethanolamine, monoisopropanolamine, 2-amino-2-methylpropanol, 2-amino-2-methyl-1,3-propanediol, 2-amino-2-ethyl-1,3-propanediol, 2-amino-2-methylbutanol, 2-aminobutanol, N,N-dimethyl ethanolamine, methylglucamine, triethanolamine, diethanolamine and triisopropanolamine, and wherein at least one alkalizing agent is a basic amino acid.

Agents containing monoethanolamine as the alkanol amine are particularly preferred.

The alkanol amine is present in oxidation coloring agents according to the invention preferably in amounts from 0.5 to 15 wt. %, particularly 2 to 5 wt. %, based on total weight of the application mixture.

An organic compound containing at least one protonizable amino group and at least one carboxylate or a sulfonate group and whose isoelectric point (pI) has a value of 7.0 or higher, measured under standard conditions, is classified as a basic amino acid within the meaning of the invention. Preferred basic amino acids are aminocarboxylic acids, particularly α-aminocarboxylic acids (alpha-aminocarboxylic acids) and ω-aminocarboxylic acids. Of the α-aminocarboxylic acids, lysine, ornithine, guanidine and arginine are particularly preferred.

Basic amino acids can preferably be added to the agents in free form. In a number of cases it is, however, also advantageous to use the amino acids in salt form. Preferred salts are then compounds with hydrohalic acids or sulfuric acid, particularly the hydrochlorides, hydrobromides and sulfates. The basic amino acids can furthermore also be used in the form of oligopeptides and protein hydrolysates, provided that they contain the required amounts of amino acids used according to the invention.

A particularly preferred basic amino acid is arginine, particularly in free form, but also used as the hydrochloride.

The basic amino acid is present in oxidation coloring agents according to the invention preferably in amounts from 0.01 to 10 wt. %, particularly 0.05 to 5 wt. %, based on total weight of the application mixture.

Agents according to the invention can furthermore contain at least one substantive dye as the color-changing component. These are dyes which attach directly to the hair and require no oxidative process to develop the color. Substantive dyes are conventionally nitrophenylene diamines, nitroaminophenols, azo dyes, anthraquinones or indophenols. Substantive dyes are each preferably used in an amount from 0.001 to 20 wt. %, based on total application preparation. The total amount of substantive dyes is preferably at most 20 wt. %. Substantive dyes are known as anionic, cationic and non-ionic substantive dyes. A further embodiment of the present invention therefore is one wherein the agent further comprises at least one substantive dye.

Preferred anionic substantive dyes are compounds known under the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue.

Preferred cationic substantive dyes are cationic triphenylmethane dyes such as Basic Blue 7, Basic Blue 26, Basic Violet 2 and Basic Violet 14, aromatic systems which are substituted with a quaternary nitrogen group such as Basic Yellow 57, Basic Red 76, Basic Blue 99, Basic Brown 16 and Basic Brown 17, as well as substantive dyes containing a heterocyclic compound having at least one quaternary nitrogen atom, particularly Basic Yellow 87, Basic Orange 31 and Basic Red 51. Cationic substantive dyes sold under the trademark Arianor are most particularly preferred cationic substantive dyes.

Non-ionic nitro and quinone dyes and neutral azo dyes in particular are suitable as non-ionic substantive dyes. Preferred non-ionic substantive dyes are compounds known under the international names or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-4-nitrophenol.

In a further embodiment of the present invention, the agents additionally contain at least one dye precursor of nature-analogous dyes.

Indoles and indolines containing at least two groups chosen from hydroxyl and/or amino groups, preferably as a substituent on the six-membered ring, are preferably used as dye precursors of nature-analogous dyes. These groups can bear further substituents, for example, in the form of an etherification or esterification of the hydroxyl group or an alkylation of the amino group. In a further embodiment, the coloring agents contain at least one indole and/or indoline derivative. Compositions according to the invention containing precursors of nature-analogous dyes are preferably used as air-oxidative coloring agents. In this embodiment, the compositions are accordingly not mixed with an additional oxidizing agent. Dye precursors of nature-analogous dyes are each preferably used in an amount from 0.001 to 5 wt. %, based on total application preparation. The total amount of substantive dyes is preferably at most 3 wt. %. Preferred indoline derivatives are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline and 5,6-dihydroxyindoline-2-carboxylic acid, in particular N-methyl-5,6-dihydroxyindoline, N-ethyl-5,6-dihydroxyindoline, N-propyl-5,6-dihydroxyindoline, N-butyl-5,6-dihydroxyindoline and particularly preferably 5,6-dihydroxyindoline. Preferred indole derivatives are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, preferably N-methyl-5,6-dihydroxyindole, N-ethyl-5,6-dihydroxyindole, N-propyl-5,6-dihydroxyindole, N-butyl-5,6-dihydroxyindole and in particular 5,6-dihydroxyindole.

It is not necessary for oxidation dye precursors, substantive dyes or nature-analogous dyes to be uniform compounds. Instead, it is possible for the individual dyes to also contain small amounts of further components arising from the manufacturing processes for the individual dyes, provided that they do not adversely influence the dyeing result or need to be excluded for other (e.g., toxicological) reasons.

For oxidative colorings, the color can develop in principle with atmospheric oxygen. However, a chemical oxidizing agent is preferably used, particularly if a lightening effect on human hair is sought in addition to the coloring. This brightening effect may be sought regardless of the dyeing method. Persulfates, peroxodisulfates, chlorites, hypochlorites and in particular hydrogen peroxide or addition products thereof with urea, melamine and sodium borate are suitable as oxidizing agents. According to the invention, however, the color-changing agent as an oxidation coloring agent can also be applied to the hair together with a catalyst, which activates oxidation of the dye precursors, for example, through atmospheric oxygen. Such catalysts include certain enzymes, iodides, quinones or metal ions.

For intense lightening of very dark hair, use of hydrogen peroxide or its addition products with organic or inorganic compounds alone is often not sufficient. In these cases a combination of hydrogen peroxide and inorganic persulfates is generally used, resulting in an increase in the lightening capacity of the agents. Preferred persulfate salts are ammonium peroxodisulfate, potassium peroxodisulfate and sodium peroxodisulfate. The peroxodisulfate salts can be included in an amount from 0.1 to 25 wt. %, particularly from 0.5 to 15 wt. %, based on total weight of the ready-to-use agent. Use of persulfate salts or peroxodisulfate salts generally takes place in the form of an optionally dedusted powder or a pressed molding.

If additional oxidizing agents are used, the actual coloring agent is conveniently prepared directly before use by mixing a preparation according to the invention containing in a cosmetic carrier at least one oxidation dye precursor and a preparation containing the additional oxidizing agent, particularly hydrogen peroxide. The agent can contain the combination of non-ionic emulsifier combination comprising at least two ethoxylated, linear fatty alcohols and the combination of interfacially active substances containing at least one anionic surfactant, at least one zwitterionic surfactant and at least one amphoteric surfactant in the preparation with oxidation dye precursors and/or in the oxidizing agent preparation. The preparation with oxidation dye precursors preferably contains a combination of non-ionic emulsifier combination comprising at least two ethoxylated, linear fatty alcohols and a combination of interfacially active substances containing at least one anionic surfactant, at least one zwitterionic surfactant and at least one amphoteric surfactant according to a first subject-matter of the invention.

Hydrogen peroxide is preferably used as the oxidizing agent. The amount of hydrogen peroxide in the ready-to-use agent is preferably 0.5 to 12 wt. %, more preferably 0.8 to 6 wt. %, based on total weight of the ready-to-use agent.

Such oxidizing agent preparations are preferably aqueous, free-flowing oxidizing agent preparations. Preparations are preferred here wherein the free-flowing oxidizing agent preparation—relative to its weight—contains 40 to 90 wt. %, preferably 50 to 85 wt. %, more preferably 55 to 80 wt. %, even more preferably 60 to 77.5 wt. %, and in particular 65 to 75 wt. % of water.

It has furthermore proved advantageous for oxidizing agent preparations, consisting in particular of oxidation coloring agents, to contain at least one stabilizer or complexing agent. Common preferred chelating agents include polycarboxylic acids, nitrogen-containing mono- or polycarboxylic acids, in particular ethylenediamine tetraacetic acid (EDTA), ethylenediamine disuccinic acid (EDDS) and nitrilotriacetic acid (NTA), geminal diphosphonic acids, in particular 1-hydroxyethane-1,1-diphosphonic acid (HEDP), aminophosphonic acids such as ethylenediamine tetra(methylene phosphonic acid) (EDTMP), diethylenetriamine penta(methylene phosphonic acid) (DTPMP), phosphonopolycarboxylic acids such as 2-phosphonobutane-1,2,4-tricarboxylic acid, and cyclodextrins, alkali stannates (sodium stannate), alkali pyrophosphates (tetrasodium pyrophosphate, disodium pyrophosphate), alkali phosphates (sodium phosphate), and phosphoric acid.

Agents according to the invention contain further auxiliary substances and additives.

It has also proved advantageous for the agents to contain additional, non-ionogenic interfacially active substances in addition to the non-ionic emulsifiers described above. Such compounds include $C_{12}$-$C_{30}$ fatty acid mono- and diesters of addition products of 1 to 30 mol of ethylene oxide with glycerol; polyglycerol esters and alkoxylated polyglycerol esters, such as for example poly(3)glycerol diisostearate and poly(2)glycerol polyhydroxystearate; alkoxylated, preferably propoxylated and in particular ethoxylated, mono-, di- and triglycerides, such as for example glycerol monolaurate+20 EO (mol of ethylene oxide) and glycerol monostearate+20 EO; amine oxides; sorbitan fatty acid esters and addition products of ethylene oxide with sorbitan fatty acid esters such as polysorbates, sorbitan monolaurate and sorbitan monolaurate+20 EO; sugar fatty acid esters and addition products of ethylene oxide with sugar fatty acid esters; addition products of ethylene oxide with fatty acid alkanol amides and fatty amines; fatty acid-N-alkyl glucamides; alkyl phenols and alkyl phenol alkoxylates having 6 to 21, particularly 6 to 15 carbon atoms in the alkyl chain and 0 to 30 ethylene oxide and/or propylene oxide units, such as nonyl phenol+4 EO, nonyl phenol+9 EO, octyl phenol+3 EO and octyl phenol+8 EO, as well as alkyl polyglycosides. Alkyl mono- and oligoglycosides and ethoxylated analogs thereof are suitable in particular as non-ionic surfactants. Such alkyl polyglycosides of the formula RO—$(Z)_x$ are preferred, wherein R consists substantially of $C_8$-$C_{18}$ alkyl groups. Any mono- or oligosaccharides such as glucose, fructose, galactose, arabinose and sucrose can be used as the sugar structural unit Z. Glucose is particularly preferred. Useful alkyl polyglycosides according to the invention contain on average 1.1 to 5 sugar units. Additional non-ionic surfactants are preferably used in a total amount from 0.1 to 45 wt. %, more preferably 1 to 30 wt. % and most preferably 1 to 20 wt. %, based on total weight of the ready-to-use agent.

Cationic surfactants of the quaternary ammonium compound, esterquat and amidoamine type are preferred. Preferred quaternary ammonium compounds are ammonium halides such as alkyltrimethylammonium chlorides, dialkyldimethylammonium chlorides and trialkylmethylammonium chlorides, as well as the imidazolium compounds known under the INCI names Quaternium-27 and Quaternium-83. Long alkyl chains of the aforementioned surfactants preferably have 10 to 18 carbon atoms. Other cationic surfactants which can be used according to the invention are quaternized protein hydrolysates. Likewise advantageous according to the invention are quaternary ester compounds known as esterquats. Esterquats are known substances containing both at least one ester function and at least one quaternary ammonium group as a structural element. Preferred esterquats are quaternized ester salts of fatty acids with triethanolamine, quaternized ester salts of fatty acids with diethanol alkyl amines and quaternized ester salts of fatty acids with 1,2-dihydroxypropyl dialkylamines (trademarks Stepantex, Dehyquart and Armocare). Cationic surfactants are present in the agents preferably in amounts from 0.05 to 10 wt. %, based on total agent. Amounts from 0.1 to 5 wt. % are particularly preferred.

Agents according to the invention can also contain additional active ingredients, auxiliary substances and additives such as non-ionic polymers, cationic polymers, zwitterionic and amphoteric polymers, anionic polymers, texturizing agents such as glucose, maleic acid and lactic acid, hair-conditioning compounds such as phospholipids, active ingredients to improve the fiber structure, particularly mono-, di- and oligosaccharides such as glucose, galactose, fructose, fruit sugar and lactose, defoaming agents such as silicones, preferably dimethicone, dyes to color the agent, anti-dandruff active ingredients, light stabilizers, proteins and protein hydrolysates, which are optionally suitably modified, active ingredients such as panthenol, pantothenic acid, pantolactone, allantoin, pyrrolidinone carboxylic acids and salts thereof as well as bisabolol, vitamins, provitamins and vitamin precursors, particularly those of groups A, $B_3$, $B_5$, $B_6$, C, E, F and H, plant extracts, fats and waxes such as beeswax, montan wax and paraffins, swelling and penetrating substances such as glycerol, propylene glycol monoethyl ether, carbonates, hydrogen carbonates, guanidines, ureas as well as primary, secondary and tertiary phosphates, opacifiers such as latex, styrene/PVP and styrene/acrylamide copolymers, pearlescent agents such as ethylene glycol mono- and distearate and PEG-3 distearate, pigments, blowing agents such as propane-butane mixtures, $N_2O$, dimethyl ether, $CO_2$ and air and antioxidants.

One skilled in the art selects these additional substances according to the desired properties of the agents. Regarding further optional components and the amounts of these components used, reference is made to relevant manuals known to one skilled in the art, for example, Kh. Schrader, Grundlagen and Rezepturen der Kosmetika, $2^{nd}$ Ed., Hüthig Buch Verlag, Heidelberg (1989).

As previously mentioned, the agents can also be prepared directly before application from two or more separately packaged preparations. This allows for separation of incompatible constituents to prevent a premature reaction. Separation into multicomponent systems is particularly appropriate in cases where there is a risk or likelihood of incompatibilities between the constituents. In such systems, the ready-to-use agent is prepared by the consumer by mixing the components directly before application. A coloring agent wherein the oxidation dye precursors are initially separate from the oxidizing agent preparation preferably containing hydrogen peroxide is preferred here.

Their specific carrier base gives the coloring agents significant advantages over the prior art in terms of their rheological properties. Agents according to the invention are particularly distinguished by high storage stability. The agents retain stable viscosity with no substantial rise and particularly no fall in viscosity, which could lead to considerable storage and application problems. This stability in viscosity applies in particular to the preparation containing the oxidation dye precursors but also to the ready-to-use agents after mixing the oxidizing agent preparation and the preparation containing the oxidation dye precursors.

Preferred agents have a viscosity of 8000 to 35,000 mPa·s, particularly 1200 to 25,000 mPa·s, measured by the Brookfield method with a number 5 spindle at 20 to 23° C. and at a rotational speed of 4 rpm.

The agents also have advantages in terms of their shear sensitivity compared to conventional agents. A relatively high shear leads to a slight rise in viscosity compared to conventional agents, in which occasionally even an undesired fall in viscosity is established, which can lead to problems with filling and storage.

The present invention secondly provides a kit of parts having at least two containers packaged separately from each other—a container (I) containing a coloring agent (A) having in a cosmetic carrier at least one oxidation dye precursor, and a further container (II) containing an aqueous oxidizing agent preparation (B) having at least one oxidizing agent, wherein coloring agent (A) contains— at least one non-ionic emulsifier combination comprising at least two ethoxylated, linear fatty alcohols each having 8 to 22 carbon atoms, at least one of the ethoxylated fatty alcohols having a moderate average degree of ethoxylation of 15 to 35 mol of ethylene oxide and at least one of the ethoxylated fatty alcohols having a high average degree of ethoxylation of 40 to 100 mol of ethylene oxide, and at least one combination of interfacially active substances comprising at least one anionic surfactant, at least one zwitterionic surfactant and at least one amphoteric surfactant.

One embodiment of this kit of parts has the characterizing feature that in the combination of interfacially active substances the weight ratio of the total amount of anionic surfactants to the total amount of amphoteric and zwitterionic surfactants has a value of from 3 to 0.3.

If a particularly intense lightening effect is desired through use of peroxodisulfate salts, it is preferable for these to be included with the kit of parts according to the invention as a separately packaged, additional component in the form of an optionally dedusted powder or a pressed molding. A container within the context of the present invention is understood to be a casing in the form of an optionally reclosable bottle, a can, a packet, a sachet or similar casings. The casing can be made from plastic, glass, (metal) sheet, card, paper or a composite.

The multicomponent kit of parts can additionally contain instructions for use. It can be further preferred if an application aid such as a comb or a brush or a mixing dish, and/or personal protection equipment such as disposable gloves, are also included with the kit.

All that has been stated regarding agents according to the invention applies with necessary alterations to further preferred embodiments of the kit of parts.

The present invention also provides a method for coloring human hair wherein an agent according to the first subject-matter of the invention is applied to the hair, left on the hair for a contact period of 2 to 30 minutes, preferably 5 to 15 minutes, and is then rinsed out of the hair.

The present invention further provides a method for coloring human hair wherein immediately prior to use an agent is produced by mixing the components of the kit of parts of the second subject-matter of the invention, the now ready-to-use agent is applied to the hair, left on the hair for a contact period of 2 to 30 minutes, preferably 5 to 15 minutes, and then rinsed out of the hair.

The short contact period in the methods according to the invention compared to commercial products likewise guarantees reduced damage to the hair through the shorter contact time between damaging substances and the hair, with the same coloring result.

Application temperatures in the coloring method according to the invention can be from 15 to 45° C. After the contact period the hair coloring agent is removed from the hair to be colored by rinsing, optionally with the aid of a shampoo. There is no need to wash with a shampoo afterwards if a carrier with high surfactant content (e.g., a coloring shampoo) was used. All that has been stated in respect of the agents according to the invention applies with necessary alterations to further preferred embodiments of the method according to the invention.

The invention also provides for use of an agent of the first subject-matter of the invention to improve the color intensity when coloring human hair.

The invention also provides for use of an agent produced by mixing the components of a kit of parts of the second subject-matter of the invention to improve the color intensity when coloring human hair.

The invention also provides for use of an agent of the first subject-matter of the invention to improve the gray coverage when coloring human hair.

The invention also provides for use of an agent produced by mixing the components of a kit of parts of the second subject-matter of the invention to improve the gray coverage when coloring human hair.

Finally it has been found that the rheological properties, particularly viscosity stability and shear sensitivity, of coloring agents can be markedly improved through the use of agents according to the invention.

The present invention therefore also provides for use of an agent of the first subject-matter of the invention to improve the rheological properties, particularly viscosity stability and shear sensitivity.

The examples below are intended to illustrate preferred embodiments of the invention without limiting it.

EXAMPLES

Production of coloring creams (amounts given in each case as percentages by weight)—

| Raw material | E1 | E2 |
|---|---|---|
| Lanette D | 12.0 | 12.0 |
| Lorol tech. | 6.0 | 6.0 |
| Eumulgin B2 | 0.5 | 0.5 |
| Eumulgin B3 | 0.5 | 0.5 |
| Mergital CS 50 A | 1.4 | 1.4 |
| Texapon NSO | 3.0 | 3.0 |
| Dehyton K | 2.0 | 2.0 |
| Amphoterge K-2 | 2.0 | 2.0 |
| 1,2-Propanediol | 1.0 | 1.0 |
| Xanthan | 0.2 | 0.2 |
| Merquat 281 | 1.5 | 1.5 |
| Ammonium sulfate, tech. pure | 2.0 | 2.0 |
| Sodium sulfite, anhydrous, 96% | 0.2 | 0.2 |
| Ascorbic acid | 0.2 | 0.2 |
| L-Arginine | 1.0 | 1.0 |
| p-Toluylene diamine sulfate | 3.50 | 1.44 |
| Resorcinol | 1.25 | 0.27 |
| 4-Chlororesorcinol | — | 0.14 |
| 2-Methylresorcinol | 0.23 | 0.32 |
| 3-Aminophenol | 0.19 | 0.12 |
| 2-Amino-3-hydroxypyridine | 0.11 | — |
| HEDP, 60% | 0.2 | 0.2 |
| Sodium silicate 40/42 | 0.5 | 0.5 |
| Monoethanolamine | 5.5 | 5.5 |
| Perfume | qs | qs |
| Water | to 100 | to 100 |

Lanette ® D $C_{16}$-$C_{18}$ fatty alcohol (INCI name: Cetearyl alcohol) (Cognis)
Lorol ® tech. $C_{12}$-$C_{18}$ fatty alcohol (INCI name: Coconut alcohol) (Cognis)
Eumulgin ® B2 $C_{16}$-$C_{18}$ fatty alcohol, ethoxylated (20 EO) (INCI name: Ceteareth-20) (Cognis)
Eumulgin ® B3 $C_{16}$-$C_{18}$ fatty alcohol, ethoxylated (30 EO) (INCI name: Ceteareth-20) (Cognis)
Mergital ® CS 50 $C_{16}$-$C_{18}$ fatty alcohol, ethoxylated (50 EO) (INCI name: Ceteareth-50) (Cognis)
Texapon ® NSO $C_{12}$ fatty alcohol sulfate, ethoxylated (2 EO) sodium salt (27% active substance; INCI name: Sodium Laureth Sulfate) (Cognis)
Dehyton ® K N,N-Dimethyl-N-(cocoalkyl amidopropyl) ammonium acetobetaine (30% active substance; INCI name: Cocamidopropyl Betaine) (Cognis)
Amphoterge ® K-2 (40% active substance; INCI name: Disodium Cocoamphodipropionate) (Lonza)
Merquat ® 281 (Dimethyl diallyl ammonium chloride/acrylic acid copolymer (40% active substance; INCI name: Polyquaternium-22) (Nalco)
Sodium silicate 40/42 Sodium silicate The fat base was melted together at 80° C. and dispersed with part of the water. The remaining formulation ingredients were then incorporated in sequence while stirring. The mixture was then made up with water to 100 wt. % and the formulation stirred until cold.

Agents according to the invention contain:
a) a combination of interfacially active substances wherein the weight ratio of the total amount of anionic surfactants (Texapon NSO; 0.81% active substance) to the total amount of amphoteric and zwitterionic surfactants (Dehyton K; 0.60% AS and Amphoterge K-2; 0.80% AS) has a value of $[0.81/(0.60+0.80)]=0.58$; and
b) a non-ionic emulsifier combination wherein the weight ratio of ethoxylated fatty alcohols having a moderate average degree of ethoxylation (Eumulgin B2 and Eumulgin B3: each 0.5% AS) to ethoxylated fatty alcohols having a high average degree of ethoxylation (Mergital CS 50, 1.4% AS) has a value of $[(0.5+0.5)/14]=0.71$.

Coloring creams E1 and E2 having high viscosity stability, particularly during storage (3 months), were obtained.

Agents in which one of the interfacially active compounds Texapon NSO, Dehyton K or Amphoterge K-2 was not incorporated exhibited markedly poorer viscosity stabilities during storage, such that their applicability was restricted.

We claim:

1. Agent for coloring keratinic fibers comprising in a cosmetic carrier:
    at least one oxidation dye precursor,
    wherein the agent further comprises:
    a) at least one non-ionic emulsifier combination comprising at least two ethoxylated, linear fatty alcohols, each having 8 to 22 carbon atoms, at least one of the ethoxylated fatty alcohols having a moderate average degree of ethoxylation of 15 to 35 mol of ethylene oxide and at least one of the ethoxylated fatty alcohols having a high average degree of ethoxylation of 40 to 100 mol of ethylene oxide, and
    b) at least one combination of interfacially active substances, containing at least one anionic surfactant, at least one zwitterionic surfactant and at least one amphoteric surfactant.

2. Agent according to claim 1, wherein the weight ratio of the combination of interfacially active substances of total anionic surfactants to total amphoteric and zwitterionic surfactants is from 3 to 0.3.

3. Agent according to claim 1, wherein the ethoxylated, linear fatty alcohol having a high average degree of ethoxylation has a high average degree of ethoxylation of 40 to 60.

4. Agent according to claim 1, wherein the weight ratio of ethoxylated fatty alcohols having a moderate average degree of ethoxylation to ethoxylated fatty alcohols having a high average degree of ethoxylation in the ready-to-use agent is 3:1 to 1:5.

5. Agent according to claim 1 further comprising from 0.005 to 1.0 wt. % of at least one polymeric thickener, based on total weight of the agent.

6. Agent according to claim 5, wherein the polymeric thickener is a thickening polysaccharide polymer.

7. Agent according to claim 1 further comprising a combination of at least two alkalizing agents,
    wherein at least one alkalizing agent is ammonia or an alkanol amine chosen from monoethanolamine, monoisopropanolamine, 2-amino-2-methylpropanol, 2-amino-2-methyl-1,3-propanediol, 2-amino-2-ethyl-1,3-propanediol, 2-amino-2-methylbutanol, 2-aminobutanol, N,N-dimethyl ethanolamine, methylglucamine, triethanolamine, diethanolamine and triisopropanolamine,
    and wherein at least one alkalizing agent is a basic amino acid.

8. Agent according to claim 7, wherein the alkanol amine is monoethanolamine.

9. Agent according to claim 7, wherein the basic amino acid is chosen from lysine, guanidine, ornithine and arginine.

10. Agent according to claim 1 further comprising at least one substantive dye.

11. Kit of parts comprising:
    a container (I) having a coloring agent (A) comprising in a cosmetic carrier at least one oxidation dye precursor, and
    a second container (II) packaged separately from container (I) and containing an aqueous oxidizing agent preparation (B) having at least one oxidizing agent,
    wherein the coloring agent (A) further comprises:
        at least one non-ionic emulsifier combination comprising at least two ethoxylated, linear fatty alcohols, each having 8 to 22 carbon atoms, at least one of the ethoxylated fatty alcohols having a moderate average degree of ethoxylation of 15 to 35 mol of ethylene oxide and at least one of the ethoxylated fatty alcohols having a high average degree of ethoxylation of 40 to 100 mol of ethylene oxide, and
        at least one combination of interfacially active substances, containing at least one anionic surfactant, at least one zwitterionic surfactant and at least one amphoteric surfactant.

12. Method for coloring human hair comprising:
    mixing the coloring agent (A) and the oxidizing agent preparation (B) of the kit of parts according to claim 11 immediately prior to use thereby producing a coloring agent,
    applying the coloring agent to the hair,
    leaving the coloring agent on the hair for a contact period of 2 to 30 minutes, and
    rinsing the coloring agent out of the hair.

13. Method of improving color intensity when coloring human hair comprising applying an agent according to claim 1 onto the hair.

14. Method of improving gray coverage when coloring human hair comprising applying an agent according to claim 1 onto the hair.

* * * * *